(12) United States Patent
Drancourt et al.

(10) Patent No.: US 8,841,087 B2
(45) Date of Patent: Sep. 23, 2014

(54) MYCOBACTERIA CULTURE MEDIUM AND METHOD INCLUDING MYCOBACTERIA OF MYCOBACTERIUM TUBERCULOSIS COMPLEX

(75) Inventors: Michel Drancourt, Marseilles (FR); Didier Raoult, Marseilles (FR)

(73) Assignee: Universite d'Aix-Marseille, Marseilles (FR)

( * ) Notice: Subject to any disclaimer, the term of this patent is extended or adjusted under 35 U.S.C. 154(b) by 196 days.

(21) Appl. No.: 13/131,921

(22) PCT Filed: Oct. 20, 2009

(86) PCT No.: PCT/FR2009/051997
§ 371 (c)(1),
(2), (4) Date: Jun. 14, 2011

(87) PCT Pub. No.: WO2010/063911
PCT Pub. Date: Jun. 10, 2010

(65) Prior Publication Data
US 2011/0262960 A1    Oct. 27, 2011

(30) Foreign Application Priority Data

Dec. 5, 2008  (FR) ...................................... 08 58311

(51) Int. Cl.
*C12N 1/20*     (2006.01)
*C12N 1/00*     (2006.01)

(52) U.S. Cl.
CPC ... *C12N 1/00* (2013.01); *C12N 1/20* (2013.01)
USPC .......................................................... 435/41

(58) Field of Classification Search
CPC .................................... C12N 1/00; C12N 1/20
USPC ............... 435/41, 71.1, 170, 404, 243, 252.1, 435/253.1
See application file for complete search history.

(56) References Cited

U.S. PATENT DOCUMENTS 2,877,161 A * 3/1959 Sebek et al. ................... 435/42
2005/0113574 A1* 5/2005 Bogatcheva et al. ............ 544/78

OTHER PUBLICATIONS

Drancourt et al. "Cost-Effectiveness of Blood Agar for Isolation of Mycbacteria", Nov. 2007.*
Production Center, BACTEC Mcyo/F Lytic Culture Vials, Feb. 2010.*
"BBL Lowenstein Jensen Medium" 2011.*
Paul R. Wheeler, et al., "Control of acyl-CoA carboxylase activity in mycobacteria", FEMS Microbology Letters, vol. 90, No. 2, Jan. 1, 1992, pp. 169-172, XP023921876.
Laurence Realini, et al., "Blood and Charcoal Added to Acidified Agar Media Promote the Growth of *Mycobacterium genavense*", Diagnostic Microbiology and Infectious Disease, vol. 34 No. 1, May 1999, pp. 45-50, XP002526451.

* cited by examiner

*Primary Examiner* — Ruth Davis
(74) *Attorney, Agent, or Firm* — Ladas & Parry LLP

(57) ABSTRACT

The present invention relates to a novel mycobacteria culture medium, particularly for mycobacteria of the *Mycobacterium tuberculosis* complex, that significantly reduces the culture isolation time and thus the time for diagnosing the mycobacteria, particularly those for tuberculosis. A culture medium according to the invention contains defibrinated blood, lecithin, and decomplemented fetal calf serum. The present invention also relates to a culture method and to a method for identifying mycobacteria, particularly bacteria of the *Mycobacterium tuberculosis* complex. The present invention also relates to a novel decontamination method through chlorhexidine treatment of biological samples in an isolation and mycobacteria culture medium, and to a method for determining by phenotype the sensitivity of mycobacteria to antibiotics by means of a solid culture medium according to the invention. Finally, the present invention also relates to a method of identification in liquid phase by mass spectrometry which reduces time for diagnosing mycobacteriosis, particularly for tuberculosis.

11 Claims, 8 Drawing Sheets

MYCOBACTERIA CULTURE MEDIUM AND METHOD INCLUDING MYCOBACTERIA OF MYCOBACTERIUM TUBERCULOSIS COMPLEX

This application is a 371 of PCT/FR2009/051997, filed on Oct. 20, 2009, which is incorporated herein by reference.

The present invention relates to a novel culture medium for mycobacteria, in particular for mycobacteria of the *Mycobacterium tuberculosis* complex, permitting a significant reduction of the times for isolation by culture and therefore of the time for diagnosing mycobacterioses, in particular tuberculosis.

The present invention also relates to a method of culture and of identification of mycobacteria and, notably, of bacteria of the *Mycobacterium tuberculosis* complex.

More particularly, the present invention relates to a novel method of decontamination of biological samples in said novel medium for isolation and culture of mycobacteria.

The present invention also relates to a rapid method for phenotypic determination of the sensitivity of a *mycobacterium*, notably of the *Mycobacterium tuberculosis* complex, to antibiotics, employing culture on a solid culture medium according to the present invention.

Finally, the present invention relates to a novel method of liquid-phase identification by mass spectrometry, contributing to significant reduction of the times for diagnosis of mycobacterioses, in particular of tuberculosis.

The mycobacteria are bacteria classified in the Actinobacteria phylum by sequencing of the 16S rRNA gene and by so-called "multilocus phylogeny" analyses [Mignard S, Flandrois J P. A seven-gene, multilocus, genus-wide approach to phylogeny of mycobacteria using supertrees. Int J Syst Evol Microbiol. 2008; 58:1432-41] and characterized by the presence of mycolic acids in their wall, which endows them with particular staining affinity (Ziehl-Neelsen staining), and by a chromosome with high G+C %>60% [Pfyffer G E. *Mycobacterium*: general characteristics, laboratory detection, in staning procedures. In: Murray Pr, Baron E J, Jorgensen J H, Landry M L, Pfaller M A. Manual of Clinical Microbiology 9th Ed. Amercian Society for Microbiology, Washington D.C.; 2007, pp. 543-572]. The bacterial genus *Mycobacterium* comprises more than sixty species, including environmental species isolated from inert environments (soil, water), species associated with animals and a strictly human species, *Mycobacterium leprae*, the causative agent of leprosy [Cole S et al. Massive gene decay in the leprosy bacillus. Nature 2001; 409:1007-11]. Certain environmental species are responsible for opportunistic infections in humans (species of the *Mycobacterium avium* complex for example) and certain species are responsible for zoonoses, in particular certain species of the *Mycobacterium tuberculosis* complex, responsible for tuberculosis.

Diagnosis of mycobacterioses is based on isolation and culture of one of the species of the genus *Mycobacterium* from a clinical sample from a human or an animal. From this standpoint, the genus *Mycobacterium* comprises a noncultivable species (*Mycobacterium leprae*), fast-growing species (*Mycobacterium fortuitum, Mycobacterium ulcerans, Mycobacterium abscessus*) giving visible colonies in less than seven days of culture and slow-growing species giving visible colonies in more than seven days of culture, or in routine practice, between 3 and 8 weeks of culture, notably with Middlebrook media. In human medicine, species of the *Mycobacterium avium* complex are detectable after 10-20 days of culture and species of the *Mycobacterium tuberculosis* complex require 10-100 viable organisms per ml of sample and 6-8 weeks of culture to obtain 100% of positive samples [Colebunders R, Bastian I. A review of the diagnosis and treatment of smear-negative pulmonary tuberculosis. Int J Tuberc Lung Dis. 2000; 4:97-107]. In view of the numerical importance and the seriousness of cases of human tuberculosis, it is in the diagnosis of tuberculosis that there have been particularly marked improvements in laboratory techniques. In fact, tuberculosis is an infectious disease in humans and animals caused by one of the seven species of the *Mycobacterium tuberculosis* complex: *Mycobacterium tuberculosis, Mycobacterium bovis* (and the BCG strains derived therefrom), *Mycobacterium africanum, Mycobacterium canettii, Mycobacterium caprae, Mycobacterium microti*, and *Mycobacterium pinnipedii* [Dye C. et al. Prospects for worldwide tuberculosis control under the WHO DOTS strategy. Lancet 1998; 352:1886-91]. The World Health Organization (WHO) estimated that tuberculosis was responsible for 9.2 million new cases and 1.6 million deaths in 2006 [World Health Organization. 2008. Global tuberculosis control: surveillance, planning, financing. WHO report. Geneva: World Health Organization. WHO/HTM/TB/2008.393]. These figures underline the importance of optimizing the microbiological diagnosis of tuberculosis in order to improve the medical management of patients and their family and friends.

The isolation and culture of mycobacteria of the *Mycobacterium tuberculosis* complex are carried out starting from clinical samples obtained from a patient showing the signs and symptoms suggestive of tuberculosis. The commonest clinical form, which is also the only clinical form that is contagious, is pulmonary tuberculosis, which is diagnosed by isolation and culture of a *mycobacterium* of the *Mycobacterium tuberculosis* complex from a respiratory sample such as sputum, bronchial aspiration, bronchoalveolar lavage fluid obtained on bronchoscopy, or pulmonary biopsy. In patients not producing sputum, gastric aspiration fluid can be used as an alternative for the isolation and culture of mycobacteria of the *Mycobacterium tuberculosis* complex in the case of pulmonary tuberculosis. There are other clinical forms of tuberculosis, in particular lymphatic tuberculosis, but also osseous tuberculoses (Pott's disease) as well as digestive-tract tuberculoses. Depending on the clinical form, different clinical samples can be sent to the laboratory for isolation and culture of mycobacteria of the *Mycobacterium tuberculosis* complex and diagnosis of the extrapulmonary forms.

Solid media, liquid media, and two-phase media having a liquid phase and a solid phase, are available for the isolation and culture of mycobacteria of the *Mycobacterium tuberculosis* complex. The solid media are manufactured on the basis of agar. Media containing whole egg are very commonly used, and the medium that is used the most is Lowenstein-Jensen medium. This medium, like the other media containing egg, contains malachite green, which helps to inhibit the growth of contaminating microorganisms. Several formulations containing variable concentrations of malachite green have been proposed, with the constant result that a decrease in the concentration of malachite green increases the ratio of contamination of the medium and an increase in the concentration of malachite green tends to decrease the isolation and culture of mycobacteria of the tuberculous group. A second category of solid media comprises the agar media and in particular Middlebrook 7H10 medium and medium 7H11 (medium 7H10 plus 0.1% of hydrolyzed casein). The Middlebrook medium contains 2% of glycerol, which facilitates culture of the mycobacteria of the *Mycobacterium avium* complex. The liquid media correspond essentially to the Middlebrook 7H9 medium.

However, isolation of the mycobacteria of the *Mycobacterium tuberculosis* complex is slow since all of the strains of the various species of the *Mycobacterium tuberculosis* complex are isolated in a time between 6 and 8 weeks. Any reduction of this time therefore represents a significant improvement of the laboratory diagnosis of tuberculosis and other *mycobacterium* infections.

After numerous attempts, a novel formulation of culture media was developed according to the present invention, permitting quicker isolation of mycobacteria of the *Mycobacterium tuberculosis* complex and of other mycobacteria, notably permitting detection and identification in less than 15 days, or even in 10 days, starting from clinical samples. The formulation of culture medium according to the invention permits isolation of mycobacteria, both in a liquid medium suitable for devices for automatic detection and in a solid medium for manual detection, and, in addition, it is compatible with decontamination with chlorhexidine in the case of clinical samples that may comprise bacteria of the commensal flora presenting a risk of inhibiting the growth of the mycobacteria.

More precisely, the present invention provides a culture medium for mycobacteria, comprising growth factors for mycobacteria and, preferably, antibiotics without activity against mycobacteria, characterized in that it comprises the following additional components:

lecithin, and defibrinated blood, and decomplemented fetal calf serum.

According to the present invention, it was therefore discovered that the combined addition of defibrinated blood, of lecithin and of decomplemented fetal calf serum met the aim of the present invention, more particularly in the case of culture and identification directly from a liquid culture broth, as will be explained below.

Fetal calf serum is a reagent that is usually employed for cell culture and isolation of intracellular microorganisms, but is not an ingredient used for the isolation of extracellular bacteria.

Fetal calf serum is decomplemented, i.e. all the proteins called "serum complement" are removed from it, in a known way, by heating, notably at 56° C. for 1 hour. This serum complement is known to have antibacterial activity.

It is to be understood that the culture medium for mycobacteria according to the invention is constituted of a basic culture medium, known for the culture of mycobacteria, notably comprising mineral salts, sugars, amino acids, proteins and vitamins, said basic culture medium being supplemented with said additional components mentioned above.

According to preferred characteristics of carrying out the invention:

lecithin is contained in a proportion by weight from 0.1 to 5%, preferably 0.5 to 1%, the lecithin is egg yolk lecithin, decomplemented fetal calf serum is contained in a proportion by volume from 2.5 to 25%, preferably from 10 to 20%, blood is contained in a proportion by volume from 2.5 to 15%, preferably from 5 to 10%, the blood is defibrinated rabbit blood or, preferably, sheep blood.

More particularly, a culture medium for mycobacteria according to the invention comprises a basic culture medium for mycobacteria comprising, besides distilled water, the following components: ammonium sulfate, magnesium sulfate, copper sulfate, zinc sulfate, sodium citrate, ferric ammonium citrate, sodium chloride, calcium chloride, monopotassium phosphate, disodium phosphate, L-glutamic acid, biotin and pyridoxine. These components are, notably, the components contained in the culture media for mycobacteria called Middlebrook media.

In practice, this culture medium is initially in the form of a lyophilisate of the components listed above, intended to be diluted in distilled water to form the culture medium according to the invention.

More particularly, said antibiotics without antimycobacterial activity are polymyxin, nalidixic acid, trimethoprim, azlocillin and vancomycin, and the culture medium further comprises an antifungal, preferably amphotericin B.

The combination of antibiotics and antifungals mentioned above, with the exception of vancomycin, constitutes the combination known by a person skilled in the art by the designation PANTA.

According to a first embodiment of the invention, said culture medium is a liquid culture medium.

More particularly, a culture medium for mycobacteria according to the invention comprises a basic culture medium which is a Middlebrook liquid medium of reference 7H9 and the following additional growth factors for mycobacteria: casein hydrolyzate, glycerol, polysorbate, hemin, lactic acid, biotin, polyoxyethylene stearate, bovine serum albumin, dextrose and preferably supplement H. Supplement H is a highly refined digestion of casein.

According to a second embodiment of a culture medium according to the invention, said culture medium is a solid culture medium containing a gelling agent preferably selected from the agars, preferably in a proportion by weight from 0.5 to 5%, more preferably from 1 to 2%.

More particularly, it is an aqueous solid medium of the Middlebrook type of reference 7H10, with addition of said gelling agent and the following additional growth factors for mycobacteria: oleic acid, bovine albumin, preferably fraction V of bovine albumin, dextrose, catalase and glycerol. Malachite green, contained in medium 7H10, is a growth inhibitor of bacteria other than mycobacteria. The aforementioned additional growth factors for mycobacteria, other than glycerol, are known by the designation OADC factors.

The present invention also supplies a method of culture of a *mycobacterium* by means of a culture medium for mycobacteria according to the invention, characterized in that a sample containing an aforementioned *mycobacterium* is incubated in an aforementioned culture medium for mycobacteria, at a temperature from 30 to 37° C., suitable for culture of the species of *mycobacterium* contained in the sample.

Most of the mycobacteria are cultured at 37° C. However, certain mycobacteria, such as *Mycobacterium marinum, Mycobacterium haemophilum, Mycobacterium ulcerans*, are cultured at a temperature from 28° C. to 30° C. *Mycobacterium szulgai* can be cultured between 25° C. and 37° C., *Mycobacterium conspicuum* is cultured between 22° C. and 31° C. The optimal temperature for growth of *Mycobacterium xenopi* and *Mycobacterium shimoidei* is 45° C. The bacteria *Mycobacterium genavense, Mycobacterium kansasii, Mycobacterium fortuitum*, the bacteria of the *Mycobacterium avium* complex, namely *Mycobacterium avium, Mycobacterium intracellulare, Mycobacterium chimaera* and *Mycobacterium colombiense* are cultured at 37° C.

More particularly, in a method of culture of a *mycobacterium* according to the invention, a sample containing a bacterium of the *Mycobacterium tuberculosis* complex is cultured at a temperature of 37° C. in an aforementioned culture medium for mycobacteria.

A method of culture of mycobacteria according to the invention can also relate to mycobacteria outside of the *Mycobacterium tuberculosis* complex, such as those mentioned above, notably *Mycobacterium marinum*, species of the *Mycobacterium avium* complex, *Mycobacterium haemophilum*, *Mycobacterium xenopi*, species of the complex *Mycobacterium abscessus*, *Mycobacterium genavense*, *Mycobacterium kansasii*, *Mycobacterium ulcerans* and *Mycobacterium fortuitum*.

Here, "bacteria of the *Mycobacterium tuberculosis* complex" means bacteria of the species *Mycobacterium tuberculosis*, *Mycobacterium bovis* and its clones or BCG subspecies, *Mycobacterium africanum*, *Mycobacterium canettii*, *Mycobacterium caprae*, *Mycobacterium microti* and *Mycobacterium pinnipedii*.

Advantageously, in a method of culture of a *mycobacterium* according to the invention, the following four stages are carried out:

culture of a biological sample that can contain mycobacteria until growth of bacteria is detectable, and identification that the bacterium detected is a bacterium of the genus *mycobacterium* by a staining test, preferably a Ziehl-Neelsen or Kinyoun staining test, and if necessary, identification of the species of said *mycobacterium* by molecular analysis, preferably by analysis of the molecular weight of the bacterial proteins by mass spectrometry.

Kinyoun staining comprises double staining with, successively, treatment with basic fushine and treatment with methylene blue. Staining is positive when there is red bacterial staining on a blue cellular background.

As explained hereunder, the means for molecular analysis can be means for analysis of bacterial proteins, notably by determination of their molecular weight by mass spectrometry. However, alternatively, it will be possible to have recourse to classical methods of molecular identification of the genome (DNA or RNA) with probes and/or amplification primers specific to different species of mycobacteria, notably as described in application WO 2008/050064. In particular, for detecting mycobacteria of the *Mycobacterium tuberculosis* complex, it will be possible to have recourse to a system called multispacer sequence typing (abbreviated hereinafter as MST) constituted of a series of fragments of nucleic acids of noncoding intergenic zones of the genome of bacteria of the *Mycobacterium tuberculosis* complex, said fragments constituting genetic markers permitting identification of different species of the *Mycobacterium tuberculosis* complex and genotyping of isolates of one and the same species of the *Mycobacterium tuberculosis* complex, and notably of the species *Mycobacterium tuberculosis*, by analysis of the sequences of said fragments of zones called MST.

Advantageously, growth of bacteria of the *Mycobacterium tuberculosis* complex is detected in less than 15 days, preferably in not more than 10 days.

Moreover, the culture media according to the invention permit detection of 50% of all of the various principal species of mycobacteria in less than a week, namely *Mycobacterium marinum*, *Mycobacterium avium*, bacteria of the *Mycobacterium tuberculosis* complex, namely the bacteria *Mycobacterium tuberculosis*, *Mycobacterium bovis*, *Mycobacterium africanum*, *Mycobacterium canettii*, *Mycobacterium caprae*, *Mycobacterium pinnipedii* and *Mycobacterium microti*.

In a preferred embodiment comprising culture of a biological sample that can contain a *mycobacterium* and contaminating bacteria whose growth can inhibit the growth of the mycobacteria, the method is characterized in that:

1/ a preliminary stage of initial decontamination of said sample is carried out in said culture medium with chlorhexidine for a limited period, in order to limit the action of the chlorhexidine to activity against bacteria other than mycobacteria, preferably about 15 minutes of treatment in a 1% chlorhexidine solution with stirring, and 2/ the chlorhexidine is removed by washing the sample thus treated from stage 1/ with a neutral buffer, followed by centrifugation and recovery of the bacterial pellet containing the contaminating bacteria thus inactivated and the mycobacteria that have not been inactivated, which is inoculated on an aforementioned culture medium for mycobacteria.

The use of chlorhexidine as decontaminating agent was limited, previously, to the decontamination of samples in solid culture media, as chlorhexidine leads to precipitation of liquid culture media. Moreover, chlorhexidine is, in principle, known to be toxic to mycobacteria. However, it was discovered according to the present invention that the presence of lecithin in the culture medium made it possible to avoid or delay the precipitation of the liquid culture medium, on the one hand, and, on the other hand, the time-limited action of chlorhexidine, by application of said washing stage 2/, makes it possible to inhibit subsequent activity of chlorhexidine against the mycobacteria. Chlorhexidine nevertheless preserves its primary activity against the bacteria of the commensal flora whose growth can inhibit the growth of the mycobacteria, called contaminating bacteria above.

This stage of preliminary decontamination is applied, in particular, for biological samples known to be carriers of a commensal flora, such as samples from sputum, from skin biopsy or stool samples, which represent 95% of biological samples available for analysis of mycobacteria. However, for biological samples such as those obtained from hemoculture or lymph node biopsy or pulmonary biopsy or bone biopsy, this decontamination is not required.

The above method is therefore particularly advantageous when said culture medium for mycobacteria is a liquid culture medium for mycobacteria.

The above method is also particularly advantageous when said biological sample is a stool sample.

In one embodiment, said culture medium is an aforementioned liquid culture medium for mycobacteria and the growth of said mycobacteria is detected by periodical analysis of the oxygen concentration within the culture vessel.

Preferably, the oxygen concentration is measured every 3 hours at most until a threshold of oxygen concentration is reached, preferably corresponding to growth of bacteria corresponding to a concentration of mycobacteria of at least $10^4$ bacteria/ml.

This method of detection of bacteria by measuring the oxygen concentration is known and devices for automatic detection are commercially available. Depending on the devices for automatic detection, the minimum concentration of mycobacteria, starting from which a significant consumption of oxygen is detected and therefore a significant drop in oxygen concentration, varies and generally corresponds to concentrations of $10^3$ to $10^4$ mycobacteria/ml.

In another embodiment, said culture medium is a solid culture medium and growth of said mycobacteria is detected with the naked eye when the formation of a colony of bacteria can be observed on said solid culture medium.

In general, observation of the formation of a bacterial colony corresponds to a concentration of bacteria of $10^6$ bacteria/ml.

In a preferred embodiment of a method according to the invention, the species of bacteria of the genus *mycobacterium* is identified by molecular analysis consisting of an analysis of the protein profile obtained by mass spectrometry, by comparing it with a series of protein profile spectra obtained with samples of reference strains of mycobacteria of different species cultured in the same culture conditions.

Here, "same culture conditions" means that the same culture medium is used at the same culture temperature for one and the same species of *mycobacterium*.

The present invention also provides a method of culture and of identification of a *mycobacterium* in a biological sample, characterized in that said biological sample is cultured in an aforementioned liquid culture medium for mycobacteria, and, for performing the mass spectrometry analysis, a bacterial pellet obtained by double centrifugation is analyzed, directly from the culture broth according to the following stages:

a- The mycobacteria in a suspension of a cultured biological sample, in which growth of bacteria has been detected, are inactivated by heating to above 90°, preferably to 95° C. for 1 hour, preferably with stirring, and b- a first centrifugation is carried out at low speed, preferably at 500 rev/min, of the supernatant of an aforementioned cultured biological sample, in which growth of bacteria has been detected, this first centrifugation being carried out until there is sedimentation of the red blood cells from the blood contained in said sample, and c- the supernatant is recovered from the first centrifugation of stage a-, and a second centrifugation is carried out at high speed, preferably at least 10 000 rev/min, preferably about 14 000 rev/min, this second centrifugation being carried out to obtain sedimentation of a bacterial pellet, and d- preferably, said bacterial pellet from stage b- is washed with a neutral buffer, such as PBS, and a chemical treatment is carried out, preferably with a mixture of acetonitrile and trifluoroacetic acid, to separate the proteins from the bacterium so that they can be analyzed by mass spectrometry, and e- the bacterial protein pellet from stage d- is recovered and is deposited on a mass spectrometry plate.

The method of inactivation in stage a- proved to be compatible with obtaining mass spectra of good quality in stage e-.

This method of identification directly from a sample of liquid media by mass spectrometry is particularly advantageous because of its rapidity, in that, in the prior art, mass spectrometry was only used for analysis of bacterial strains taken directly from a solid medium. Thus, in the case of a clinical sample cultured in a liquid medium, the bacteria were reinoculated and then cultured on a solid medium before being taken for identification by mass spectrometry, which took an additional time of 3 to 8 weeks, depending on the type of mycobacteria, in particular from 6 to 8 weeks of culture on said solid medium for bacteria of the *Mycobacterium tuberculosis* complex.

According to the present invention, analysis by mass spectrometry can be carried out directly from a bacterial pellet obtained directly from the liquid culture medium.

In total, taking account of the time of the heating stages and of the centrifugation stages a- to e- above, it is possible to obtain the protein analysis spectrum by mass spectrometry about 1.5 h after detecting growth of said bacteria by culture, which, as mentioned above in the case of mycobacteria of the *Mycobacterium tuberculosis* complex, can be obtained in not more than about 15 days, or even 10 days.

The present invention also relates to a rapid method for phenotypic determination of the sensitivity of mycobacteria, notably of *Mycobacterium tuberculosis*, to antibiotics.

The treatment of tuberculosis is based on polychemotherapy combining five antibiotics, rifampicin, isoniazid, ethambutol and pyrazinamide which are called, with streptomycin, first-line antituberculous drugs. Throughout the world, there has been emergence of strains of *M. tuberculosis* called "multi-drug resistant" (MDR-TB) resistant to rifampicin and to isoniazid and resistant and extensively resistant strains (XDR-TB) which are MDR-TB strains that are also resistant to second-line antituberculous drugs (fluoroquinolones, aminoglycosides, capreomycin) [Gagneux S. Clin Infect Dis. 2009; 15: S1:66-68]. In France, their prevalence is estimated at 15%. The term "primary resistance" refers to a resistant strain isolated from a patient who has never received antituberculous treatments, and the term "secondary resistance" refers to the resistant strain isolated from a patient who has had the benefit of antituberculous treatment prior to isolation of the strain [Schluger N W, Up-to-date 2009].

The resistant strains of the *Mycobacterium tuberculosis* complex pose a therapeutic problem as they require the administration of second-line antituberculous antibiotics, which have the following drawbacks:

(1) they are less effective than the first-line antituberculous antibiotics, (2) they must be administered parenterally in contrast to the first-line antituberculous antibiotics, (3) they are more toxic than the first-line antituberculous antibiotics.

As the prognosis of tuberculosis is linked to the administration of effective antibiotics, it is absolutely essential to determine, with the shortest possible delay, the sensitivity of the strains to the antituberculous drugs (antibiogram). The genotypic methods that detect the presence of mutations in target genes is based on technology and expertise that is not widely available [Woods G L, Warren N G, Inderlind C B. Susceptibility test methods: Mycobacteria, Nocardia, and other actinomycetes in: Annual of Clinical Microbiology, 9th edition (Nurray P R, Baren E J, Jorgensen J H, Bry N L, Psaller M A. American Society for Microbiology, 2007, page 1223-1247]. For antibiotics other than rifampicin, the statistical association between mutations of the target gene and phenotype of resistance is low. That is why there is such interest in phenotypic tests. The latter can be automated in a liquid medium; but this technique only allows testing one or two concentrations of antibiotic per strain and tolerates the confusion between resistant and contaminating strain of *M. tuberculosis* [Anthony R M et al. Int J Tuberc Lung Dis. 2009; 13:1051-1053]. It is therefore preferable to carry out the tests in a solid medium, permitting discrimination of contaminating colonies. These tests are based on observation of inhibition of growth of the *M. tuberculosis* complex in the presence of a known concentration of antibiotic, relative to a control with growth without antibiotic. The current limits of the phenotypic tests in a solid medium are the delay of 3-4 weeks for obtaining the result and manipulation of large amounts of *M. tuberculosis* (a class 3 pathogen) corresponding to one medium per concentration of antibiotic tested.

A solid culture medium according to the present invention makes it possible to reduce the time for growth of the colonies of *M. tuberculosis* in the presence of antibiotic and therefore quickly obtain antibiogram results. Moreover, it was discovered according to the present invention that it was possible to use advantageously the E-test method for conducting antibiograms of *M. tuberculosis*. The E-test (AB Biodisk, Solna, Sweden; BioMérieux, Marcy-l'Etoile, France) consists of a strip of paper impregnated with a concentration gradient of an antibiotic under investigation, giving direct reading of the concentration causing inhibition of growth of the bacterium (Minimum Inhibitory Concentration, MIC). The E-test has been validated for *M. tuberculosis* on reference media different from that according to the invention [Esteban J. et al. Eur J Clin Microbiol Infect Dis 2005; 24: 856-857] and the characteristics of the solid culture medium according to the invention did not allow prediction of whether it would be suitable for carrying out E-tests.

It has been shown according to the present invention that the solid culture medium according to the invention also permits quicker execution and easier reading of a phenotypic test of antibiotic sensitivity and resistance of the *Mycobacterium tuberculosis* complex than the standard media.

The present invention therefore provides a medium for isolation and rapid growth of the *Mycobacterium tuberculosis* complex, for the rapid execution of phenotypic tests of the sensitivity of the *Mycobacterium tuberculosis* complex to antituberculous antibiotics, as illustrated in the example.

More precisely, the present invention supplies a method of culture permitting rapid phenotypic determination of the sensitivity of a *mycobacterium* to antibiotics, according to which the following stages are carried out:

i/- culture of an aforementioned *mycobacterium*, preferably of the *Mycobacterium tuberculosis* complex, on said solid culture medium in the presence of at least one given antibiotic, at different known concentrations, and ii/- determination of the lowest concentration of antibiotic, preferably selected from rifampicin, isoniazid, ethambutol, pyrazinamide and streptomycin, that inhibits all visible growth of said bacterium (MIC: minimum inhibitory concentration).

Thus, as is known, for each *mycobacterium*-antibiotic pair, a minimum inhibitory concentration or MIC can be determined and compared with the critical concentrations of antibiotics that a patient can receive without risk and that blocks the growth of the bacterial strain in question. Then the sensitivity or the resistance of the bacterium to the antibiotic is determined as follows:

if the MIC is below the lower critical concentration, the bacterium is sensitive to the antibiotic, and if the MIC is above the upper critical concentration, the bacterium is resistant to the antibiotic in question.

In a preferred embodiment of the invention, in stage i/-, at least one strip of paper impregnated with an aforementioned antibiotic, at different concentrations according to a concentration gradient along said strip, is placed on said solid culture medium.

More particularly, a Petri dish comprising said solid culture medium according to the invention is seeded at a concentration of at least $10^4$ colonies/ml, preferably $10^6$ colonies/ml, then an aforementioned strip is placed on said solid culture medium, notably a strip of the E-test type that comprises a continuous gradient of increasing concentrations of antibiotic from end to end of said strip, said concentrations of antibiotic being written directly on the strip, and the dish with the strip thereon is incubated and the MIC is read at the intersection of the disk of inhibition of bacterial growth with the strip.

According to other known methods of application, the strip can be replaced with a disk of blotting paper impregnated with the critical concentration of antibiotic, in order to verify the existence of a zone of inhibition around the disk to establish that the strain is sensitive to the antibiotic.

According to another known variant of application, the antibiotic can be incorporated directly in the mass of said solid culture medium at said critical concentration and the growth of the strain on said solid culture medium impregnated with said antibiotic can be compared with the growth of one and the same strain on one and the same solid culture medium not containing antibiotic, to verify the presence or absence of bacterial growth in the culture medium with or without antibiotic and deduce that the strain is sensitive to the antibiotic if less growth of the strain is observed in the solid culture medium containing said antibiotic.

Other characteristics and advantages of the present invention will become clearer on reading the examples given below, referring to FIGS. 1 to 7, in which.

EXAMPLE 1

Figure 1:
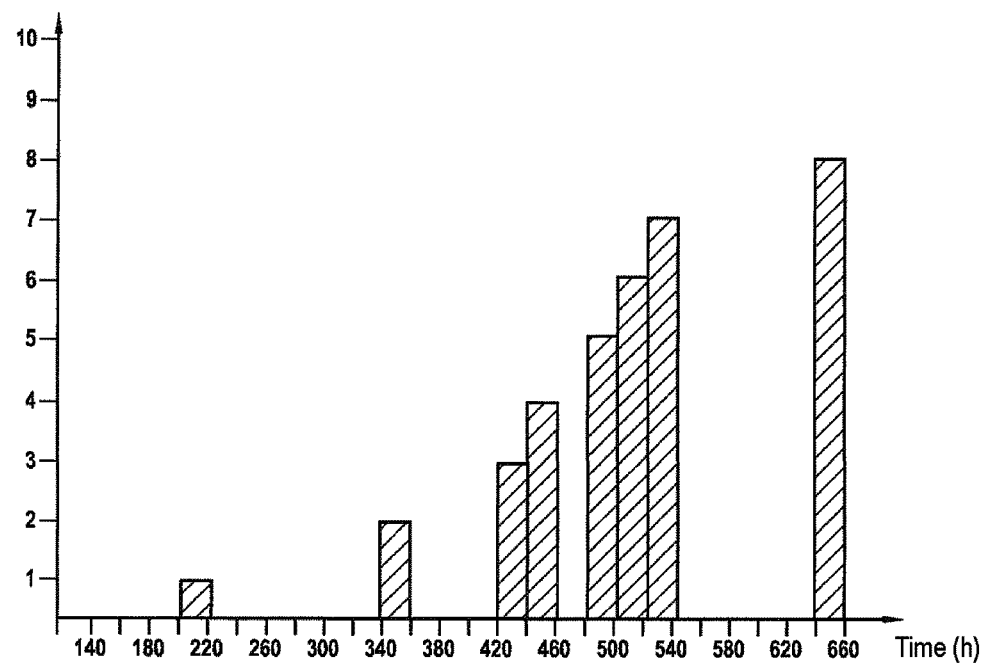
FIGS. 1 to 4 show graphs representing the cumulative time T (in hours) for detecting a number of bacteria, indicated from 1 to 10, of 10 strains of *Mycobacterium tuberculosis* for a reference culture medium (FIG. 1) and culture media according to the invention (FIGS. 2 to 4)
Figure 2:
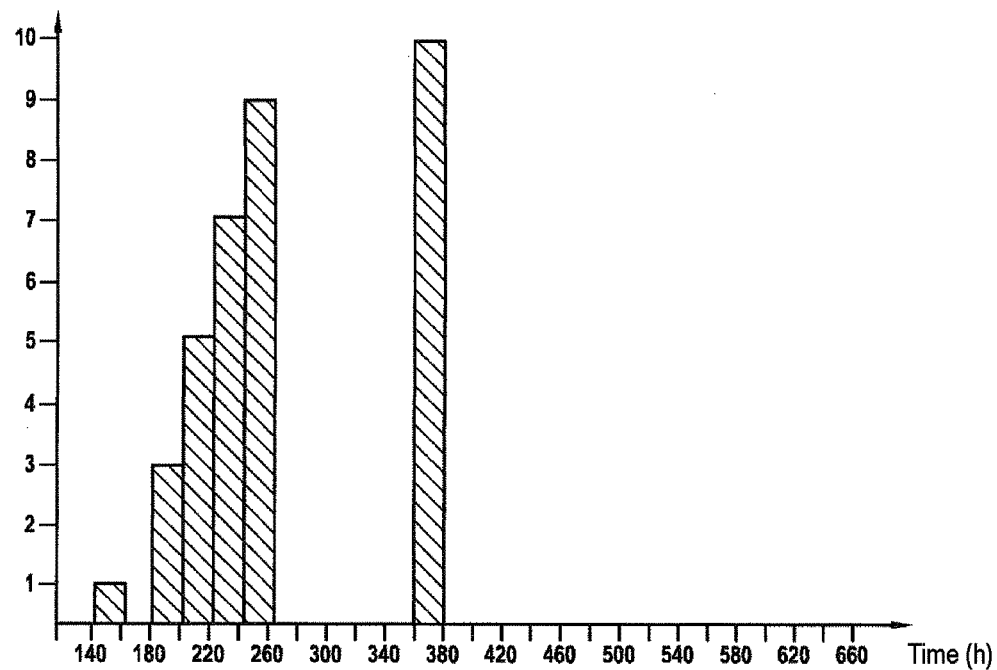
Figure 3:
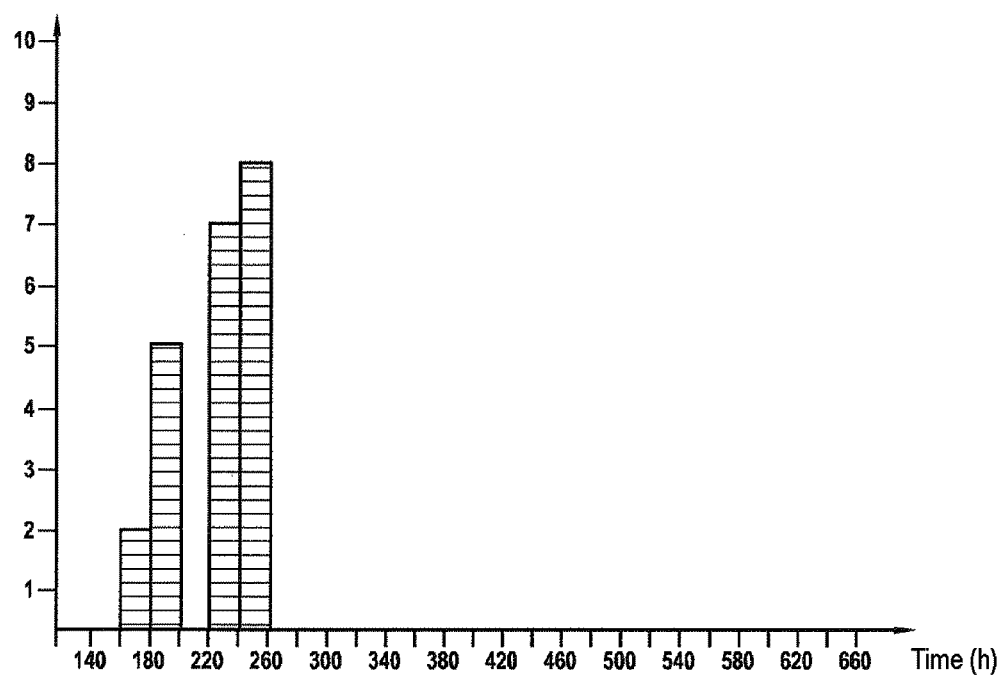
Figure 4:
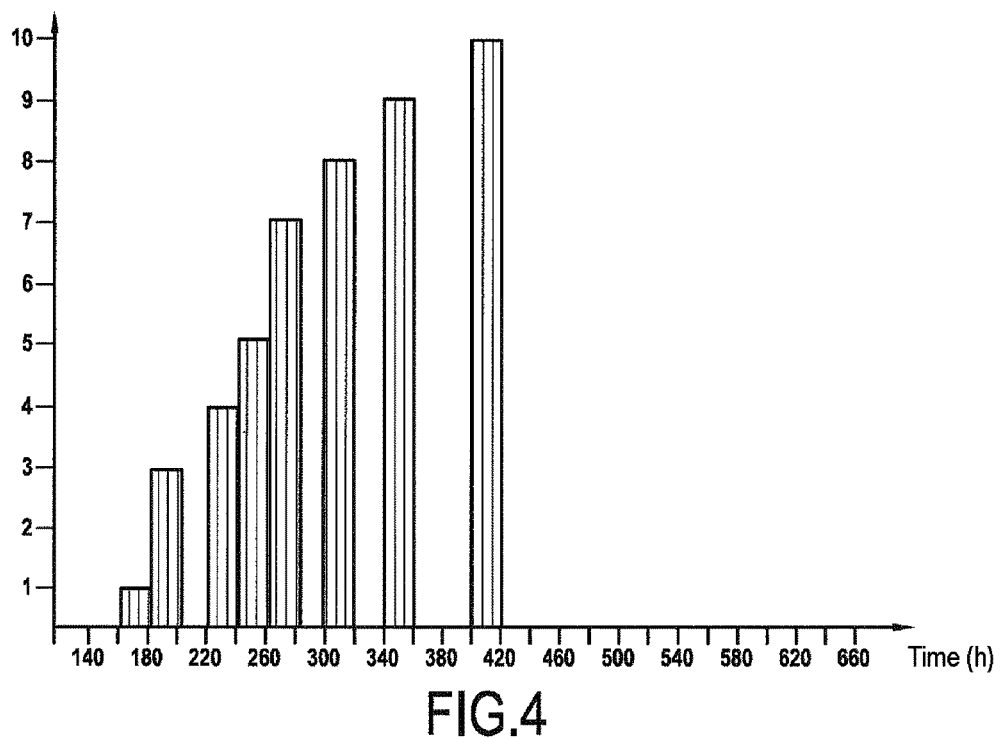
Figure 5:
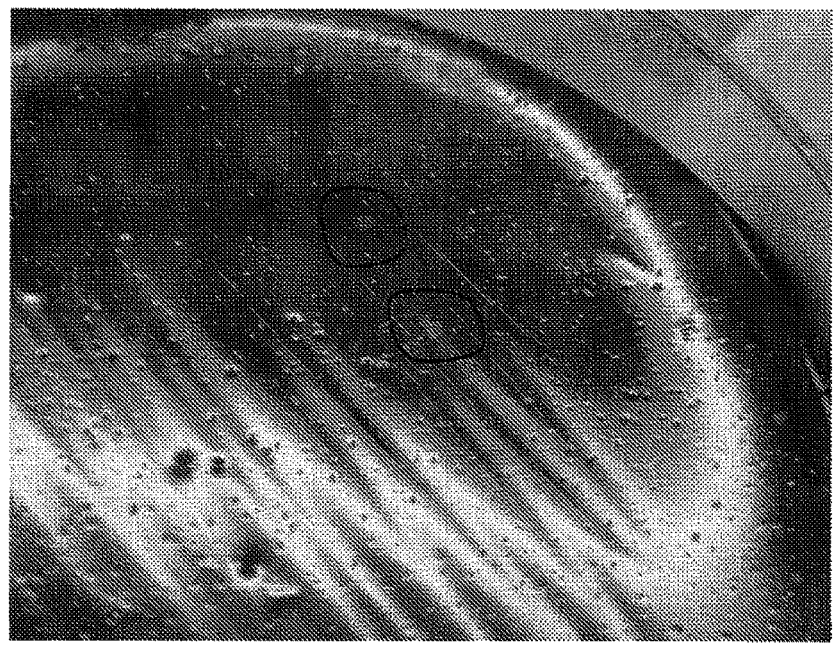
FIG. 5 shows a photograph of two colonies of mycobacteria cultured on solid medium according to example 2.
Figure 6:
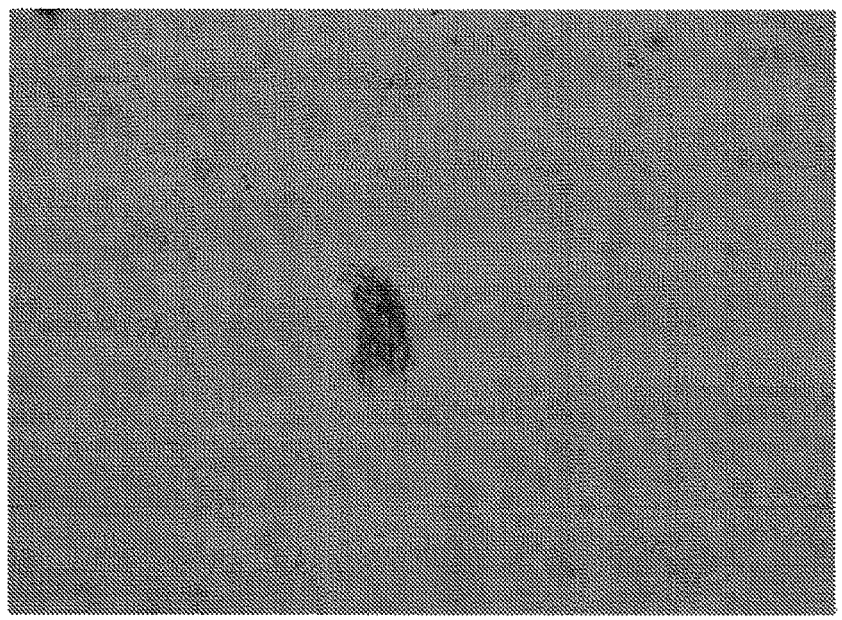
FIG. 6 shows a photograph of Ziehl-Neelsen staining of a colony cultured on solid medium in example 2.

Culture of Mycobacteria of the Tuberculous Group in Liquid Media

In this example, the inventors inoculated strains of *Mycobacterium tuberculosis* in parallel in Middlebrook 7H9 reference medium with supplements F and PANTA (Becton-Dickinson, Grenoble, France) and in one of the three media of their invention, the composition of which is given below for a bottle of 40 ml in which volume the tests were performed:

EXAMPLE 1A

Final Composition of Medium B25% (for 1000 ml)

1- Middlebrook 7H9 Medium
Sterile distilled water: 750 ml
Ammonium sulfate: 1 g
L-glutamic acid: 0.5 g
Sodium citrate: 0.1 g
Pyridoxine: 1 mg
Biotin: 0.5 mg
Disodium phosphate: 2.5 g
Monopotassium phosphate: 1 g
Ferric ammonium citrate: 0.1 g
Magnesium sulfate: 0.05 g
Calcium chloride: 0.5 mg
Zinc sulfate: 1 mg
Copper sulfate: 1 mg
Casein hydrolyzate: 1 g
Supplement H: 3 g
Glycerol: 1 g
Polysorbate 80: 0.05 g
Hemin: 0.005 g
2- Additional Growth Factors:
Lactic acid: 168 mg
Polyoxyethylene stearate: 110 mg
Bovine serum albumin: 5.6 g Dextrose: 1100 mg
Biotin: 0.57 mg
3- Antibiotics Without Antimycobacterial and Antifungal Activities:
Polymyxin: 40 000 units
Nalidixic acid: 16 mg
Trimethoprim: 4 mg
Azlocillin: 4 mg
Vancomycin: 20 mg
Amphotericin B: 4 mg
4- Additional Components of the Invention:
Decomplemented fetal calf serum: 250 ml
Defibrinated sheep blood: 50 ml
Lecithin: 0.5 g

EXAMPLE 1B

Final Composition of Medium C15% (for 1000 ml)

1- Middlebrook 7H9 Medium
Sterile distilled water: 750 ml
Ammonium sulfate: 1 g
L-glutamic acid: 0.5 g
Sodium citrate: 0.1 g
Pyridoxine: 1 mg
Biotin: 0.5 mg
Disodium phosphate: 2.5 g
Monopotassium phosphate: 1 g
Ferric ammonium citrate: 0.1 g
Magnesium sulfate: 0.05 g
Calcium chloride: 0.5 mg
Zinc sulfate: 1 mg
Copper sulfate: 1 mg
Casein hydrolyzate: 1 g
Supplement H: 3 g
Glycerol: 1 g
Polysorbate 80: 0.05 g
Hemin: 0.005 g
2- Additional Growth Factors:
Lactic acid: 168 mg
Polyoxyethylene stearate: 110 mg
Bovine serum albumin: 5.6 g
Dextrose: 1100 mg
Biotin: 0.57 mg
3- Antibiotics Without Antimycobacterial and Antifungal Activity
Polymyxin: 40 000 units
Nalidixic acid: 16 mg
Trimethoprim: 4 mg
Azlocillin: 4 mg
Vancomycin: 20 mg
Amphotericin B: 4 mg
4- Additional Components of the Invention:
Decomplemented fetal calf serum: 150 ml
Defibrinated sheep blood: 50 ml
Lecithin: 0.5 g
EXAMPLE 1C: Final Composition of Medium D5% (for 1000 m)
1- Middlebrook 7H9 medium:
Sterile distilled water: 750 ml
Ammonium sulfate: 1 g
L-glutamic acid: 0.5 g
Sodium citrate: 0.1 g
Pyridoxine: 1 mg
Biotin: 0.5 mg
Disodium phosphate: 2.5 g
Monopotassium phosphate: 1 g
Ferric ammonium citrate: 0.1 g
Magnesium sulfate: 0.05 g
Calcium chloride: 0.5 mg
Zinc sulfate: 1 mg
Copper sulfate: 1 mg
Casein hydrolyzate: 1 g
Supplement H: 3 g
Glycerol: 1 g
Polysorbate 80: 0.05 g
Hemin: 0.005 g
2- Additional Growth Factors:
Lactic acid: 168 mg
Polyoxyethylene stearate: 110 mg
Bovine serum albumin: 5.6 g
Dextrose: 1100 mg
Biotin: 0.57 mg
3- Antibiotics Without Antimycobacterial and Antifungal Activity:
Polymyxin: 40 000 units
Nalidixic acid: 16 mg
Trimethoprim: 4 mg
Azlocillin: 4 mg
Vancomycin: 20 mg
Amphotericin B: 4 mg
4- Additional Components of the Invention:
Decomplemented fetal calf serum: 50 ml
Defibrinated sheep blood: 50 ml
Lecithin: 0.5 g In this example, ten clinical strains of *Mycobacterium tuberculosis* were inoculated in parallel in a control medium A0% and in three media of the invention designated B25%, C15% and D5%. These ten strains comprised six strains sensitive to antituberculous antibiotics, a *Mycobacterium tuberculosis* strain No. 9 resistant to streptomycin and to isoniazid, a *Mycobacterium tuberculosis* strain No. resistant to streptomycin and to Rifadin and two *Mycobacterium tuberculosis* strains No. 11 and No. 12 resistant to streptomycin, to rifampicin, to ethambutol and to isoniazid (so-called multidrug-resistant MDR strains). For one and the same strain, the same inoculum was seeded in parallel in the four media. The liquid media were prepared in glass bottles incubated in a BACTEC 9000MB automatic incubator (Becton-Dickinson, Grenoble, France) at a constant temperature of 37° C. The experiment was repeated three times with the same strains. The automatic incubator detects the presence of oxygen consumption in the bottles, an indicator of bacterial growth, and shows the time between said detection and placing the bottle in the automatic incubator. This time is the criterion used in this example. The assessment criterion in this example is therefore the time taken for growth of identified mycobacteria to be detected by the BACTEC 9000MB automatic incubator.

In this example, the specificity of detection of mycobacteria by the automatic incubator was confirmed after Gram staining of the supernatant from the bottle (to verify absence of contaminating bacterium), after Kinyoun staining of the supernatant from the bottle (to verify presence of alcohol-acid-resistant bacilli, characteristic of the mycobacteria) then by real-time PCR amplification of the insertion sequence IS6110 specific to the bacteria of the *Mycobacterium tuberculosis* complex.

Kinyoun staining was carried out according to the following protocol: After preparing a cytospin slide, the slide is immersed in methanol for 10 min, then it is immersed in a Kinyoun solution (basic Fushine 40 g, phenol 80 ml, ethyl alcohol 200 ml, water for a final volume of one liter) for three hours. After rinsing with water, the slide is covered with Gabett solution (Methylene blue 10 g, sulfuric acid 60° B 200 ml, absolute alcohol 300 ml and water for a final volume of 500 ml) for five minutes, rinsed with water, dried and read with a light microscope at ×1000 magnification. Staining is positive when there is red bacterial staining on a blue cellular background.

The insertion sequence IS6110, specific to bacteria of the *Mycobacterium tuberculosis* complex is described in [van Embden J D et al. Strain identification of *Mycobacterium tuberculosis* by DNA Fingerprinting: recommendation for a standardized methodology. J. Clin. Microbiol. 1993; 31:406-409].

The inventors also observed that addition of 5%, 15% or 25% of defibrinated sheep blood did not induce $O_2$ consumption detected by the automatic incubator and therefore no false positive; this experiment was conducted three times.

The inventors have thus tested standard strains of several species of the genus *Mycobacterium* obtained from public collections as well as some clinical strains resulting from the diagnostic activity of their laboratory including a strain of *M. marinum*.

The standard strains were: *M. tuberculosis* H37RV, *M. bovis* CIP 105050, *M. bovis* BCG vaccinia CIP 105060, *M. africanum* CIP 105147$^T$, *M. pinnipedii* CIP 7177, *M. avium* ss paratuberculosis ATCC 19698$^T$.

The time for detection is always reduced in the case of culture with the culture media according to the invention in comparison with a Middlebrook 7H9 medium, notably from 375 to 55 hours for *Mycobacterium africanus*, from 336 to 29 hours for *Mycobacterium pinnipedii* and from 450 to 35 hours for *Mycobacterium bovis*.

For the species *Mycobacterium tuberculosis*, the inventors took care to test clinical strains sensitive to antituberculous drugs and clinical strains resistant to certain antituberculous drugs.

Results from these tests are given in the graphs in FIGS. 1 to 4, which show, on the ordinate, a number of strains of different species of the *Mycobacterium tuberculosis* complex and, on the abscissa, the cumulative time expressed in hours (t) for detection of the number of strains shown on the ordinate of up to ten strains of different species of the *Mycobacterium tuberculosis* complex for each of the three culture media of the invention (media B25% (FIG. 2), C15% (FIG. 3) and D5% (FIG. 4)) relative to the reference medium A0% (FIG. 1).

These graphs show:

1/- the superiority of the culture media of the invention for culture of *Mycobacterium tuberculosis*, since the culture time for observing detection of bacterial growth is less in the media of the invention relative to the reference medium, 2/- the fact that the culture media of the invention permit culture of the strains of *Mycobacterium tuberculosis* independently of their profile of resistance to antituberculous antibiotics.

Detection of bacterial growth was always possible in less than 15 days, or even less than 10 days.

Moreover, the median time permitting detection of 50% of the strains inoculated is less than or equal to one week, with the culture media according to the invention.

EXAMPLE 2

Culture of Mycobacteria in Solid Medium

In this example, the inventors inoculated different agar-containing solid media in parallel with three clinical strains of *Mycobacterium tuberculosis*. The media were (1) Middlebrook 7H10 plus agar 0.5% (2) Middlebrook 7H10 plus agar 1% plus 5% of defibrinated sheep blood plus 5% of fetal calf serum plus 0.5% of egg lecithin (3) Middlebrook 7H10 plus agar 0.5% plus 5% of defibrinated sheep blood plus 15% of fetal calf serum plus 0.5% of egg lecithin (4) Middlebrook 7H10 plus agar 0.5% plus 5% of defibrinated sheep blood plus 25% of fetal calf serum plus 0.5% of egg lecithin. Two control agars were used systematically in parallel, an agar Middlebrook 7H10 plus agar 1% and an agar Middlebrook 7H10 plus agar 1% plus 5% of defibrinated sheep blood plus 5% of fetal calf serum plus 0.5% of egg lecithin. The control agars (not inoculated) and the inoculated agars were incubated at 37° C. in an atmosphere containing 5% $CO_2$ in plastic bags preventing dehydration. The agars were inspected daily.

The assessment criterion used in this example is the time for appearance of colonies detected by naked-eye inspection of the agars and confirmed as being colonies of *Mycobacterium tuberculosis* by Ziehl-Neelsen staining and sequencing.

The solid media used have the following composition:

For definite confirmation of the appearance of colonies, the inventors photographed said colonies. The inventors then performed Kinyoun staining on a sample from said colony, and away from that, from a region of the same agar without a colony. In all cases, no alcohol-acid-resistant bacilli were detected away from the colony, whereas said bacilli were detected in the colonies.

An example of colonies is shown in FIG. 6.

FIG. 5 shows an agar containing medium C15% inoculated 10 days previously with a clinical strain of *Mycobacterium tuberculosis*, showing two colonies (circles).

FIG. 6 shows Ziehl-Neelsen staining performed on a colony obtained in 10 days from a clinical strain of *Mycobacterium tuberculosis* on solid medium C15%.

EXAMPLE 2A

Solid Medium B25% for 1000 ml

1- Middlebrook 7H10 Medium:
Sterile distilled water: 750 ml
Ammonium sulfate: 0.50 g
Monopotassium phosphate: 1.50 mg
Disodium phosphate: 1.50 g
Sodium citrate: 0.4 g
Magnesium sulfate: 0.025 g
Calcium chloride: 0.00050 g
Zinc sulfate: 0.0010 g
Copper sulfate: 0.0010 g
L-glutamic acid: 0.50 g
Ferric ammonium citrate: 0.04 g
Pyridoxine hydrochloride: 0.0010 g
Biotin: 0.000050 g
Malachite green: 0.0000250 g
Agar: 15 g
2- Additional Growth Factors
Sodium chloride: 8.50 g
Bovine albumin (fraction V): 50 g
Dextrose: 20 g
Catalase: 0.030 g
Oleic acid: 0.60 ml
Glycerol: 0.5%
3- Antibiotics Without Antimycobacterial and Antifungal Activity:
Polymyxin: 40 000 units
Amphotericin B: 4 mg
Nalidixic acid: 16 mg
Trimethoprim: 4 mg
Azlocillin: 4 mg
Vancomycin: 20 mg 4- Additional Components of the Invention:
Decomplemented fetal calf serum: 250 ml
Defibrinated sheep blood: 50 ml
Lecithin: 0.50 g

EXAMPLE 2

Solid Medium C15% for 1000 ml

1- Middlebrook 7H10 medium:
Sterile distilled water: 750 ml
Ammonium sulfate: 0.50 g
Monopotassium phosphate: 1.50 mg
Disodium phosphate: 1.50 g
Sodium citrate: 0.4 g
Magnesium sulfate: 0.025 g
Calcium chloride: 0.00050 g
Zinc sulfate: 0.0010 g
Copper sulfate: 0.0010 g
L-glutamic acid: 0.50 g
Ferric ammonium citrate: 0.04 g
Pyridoxine hydrochloride: 0.0010 g
Biotin: 0.000050 g
Malachite green: 0.0000250 g
Agar: 15 g
2- Additional Growth Factors:
Sodium chloride: 8.50 g
Bovine albumin (fraction V): 50 g
Dextrose: 20 g
Catalase: 0.030 g
Oleic acid: 0.60 ml
Glycerol: 0.5%
3- Antibiotics Without Antimycobacterial and Antifungal Activity:
Polymyxin: 40.000 units
Amphotericin B: 4 mg
Nalidixic acid: 16 mg
Trimethoprim: 4 mg
Azlocillin: 4 mg
Vancomycin: 20 mg
4- Additional Components of the Invention:
Decomplemented fetal calf serum: 150 ml
Defibrinated sheep blood: 50 ml
Lecithin: 0.50 g

EXAMPLE 2C

Solid Medium D5% for 1000 ml

1- Middlebrook 7H10 Medium:
Sterile distilled water: 750 ml
Ammonium sulfate: 0.50 g
Monopotassium phosphate: 1.50 mg
Disodium phosphate: 1.50 g
Sodium citrate: 0.4 g
Magnesium sulfate: 0.025 g
Calcium chloride: 0.00050 g
Zinc sulfate: 0.0010 g
Copper sulfate: 0.0010 g
L-glutamic acid: 0.50 g
Ferric ammonium citrate: 0.04 g
Pyridoxine hydrochloride: 0.0010 g
Biotin: 0.000050 g
Malachite green: 0.0000250 g
Agar: 15 g
2- Additional Growth Factors:
Sodium chloride: 8.50 g
Bovine albumin (fraction V): 50 g
Dextrose: 20 g
Catalase: 0.030 g
Oleic acid: 0.60 ml
Glycerol: 0.5%
3- Antibiotics Without Antimycobacterial and Antifungal Activity:
Polymyxin: 40.000 units
Amphotericin B: 4 mg
Nalidixic acid: 16 mg
Trimethoprim: 4 mg
Azlocillin: 4 mg
Vancomycin: 20 mg
4- Additional Components of the Invention:
Decomplemented fetal calf serum: 50 ml
Defibrinated sheep blood: 50 ml
Lecithin: 0.50 g

EXAMPLE 3

Decontamination of the Mycobacteria and Culture in Liquid Medium

The mycobacteria must be isolated and cultured from clinical samples normally contaminated with a commensal flora, for example in the case of sputum samples, which are the commonest in the laboratory, or in stool samples. Several methods of decontamination have been proposed in the literature. They essentially comprise decontamination with sodium hydroxide. Pretreatment with 2% N-acetyl-L-cysteine mixed with dithiothreitol makes it possible to reduce the final concentration of sodium hydroxide to between 1% and 2%. The experience of the inventors concerning isolation of mycobacteria of the *Mycobacterium tuberculosis* complex, notably from stool samples, is that this protocol does not provide satisfactory decontamination, notably of stool samples. The inventors therefore tested another protocol based on the use of chlorhexidine, decontamination used for isolation of mycobacteria outside of the *Mycobacterium tuberculosis* complex from respiratory samples in patients with mucoviscidosis [Ferroni A, Vu-Thien H, Lanotte P, Le Bourgeois M, Sermet-Gaudelus I, Fauroux B, Marchand S, Varaigne F, Berche P, Gaillard J L, Offredo C. Value of the chlorhexidine decontamination method for recovery of nontuberculous mycobacteria from sputum samples of patients with cystic fibrosis. J Clin Microbiol. 2006; 44:2237-9]. However, this method is performed during inoculation of solid media containing egg (Lowenstein-Jensen medium, Coletsos medium for example), but is not used in liquid culture media. However, the inventors discovered that the liquid culture media according to the invention are compatible with chlorhexidine decontamination for inactivating the contaminating bacteria that inhibit growth of mycobacteria, without inhibiting the growth of mycobacteria as described below.

Starting from chlorhexidine digluconate at 20% (Sigma, Illkirch, France), the inventors prepared and used 1% chlorhexidine digluconate by extemporaneous dilution in sterile distilled water. The diluted chlorhexidine keeps for 24 hours.

The decontamination protocol was as follows:
prepare 5 ml of sample in a 50-ml Falcon tube add 3 volumes (i.e. 15 ml) of 1% chlorhexidine digluconate
vortex
stir at room temperature on a stirrer for 15 min
add 30 ml of phosphate buffer pH 6.8 agitate by inversion
centrifuge for 20 min at 3500 rev/min
decant the supernatant
take up the pellet in 500 µl of phosphate buffer pH 6.8
vortex
seed at a rate of 200 to 300 µl of this suspension per bottle.

This protocol was applied successfully to a clinical strain of *Mycobacterium gordonae*, used as control strain for the whole *Mycobacterium* genus.

EXAMPLE 4

Isolation of Mycobacteria by Culture of Clinical Samples in Liquid Medium

In this example, the inventors compared the medium of their invention in parallel with the reference medium, for isolation of *Mycobacterium tuberculosis* mycobacteria from clinical samples showing presence of alcohol-acid-resistant bacilli after Ziehl-Neelsen staining. It is known from the medical literature that the presence of alcohol-acid-resistant bacilli is evidence of an inoculum $\geq 10^4$ mycobacteria/mL of sample [Hobby G L, Holman A P, Iseman M D, Jones J M. Enumeration of tubercle bacilli in sputum of patients with pulmonary tuberculosis. Antimicrob Agents Chemother. 1973; 4:94-104].

In this example, the inventors inoculated various clinical samples displaying alcohol-acid-resistant bacilli suggestive of mycobacteria decontaminated with sodium hydroxide, in parallel in a Middlebrook 7H9 medium with addition of a mixture of antibiotics and amphotericin B (antifungal) marketed by Becton-Dickinson with the acronym PANTA and in a culture broth from example 1, comprising a Middlebrook medium 7H9-PANTA plus 5% of defibrinated sheep blood, 25% of decomplemented fetal calf serum plus 0.5% of egg lecithin. The media were contained in bottles incubated in parallel in a BACTEC 9000MB automatic incubator at 37° C. with detection of oxygen consumption as explained above. Confirmation of the presence of mycobacteria and their identification were carried out as explained above.

The assessment criterion used is the time for detection of growth of mycobacteria by a BACTEC 9000MB automatic incubator.

A bronchial aspiration sample was detected by culture in 3.22 days in Middlebrook 7H9 plus blood against 5 days in Middlebrook 7H9; a sputum sample was detected by culture in 8 days in Middlebrook 7H9 plus blood and in 13 days in Middlebrook 7H9; a bronchioloalveolar lavage sample was detected by culture in 4.52 days in Middlebrook 7H9 plus blood and in 7.34 days in Middlebrook 7H9. This example illustrates the superiority of the culture medium of the invention for isolation of mycobacteria, in particular of mycobacteria of the *Mycobacterium tuberculosis* complex.

This constitutes a result that is of great importance for the time for diagnosis of tuberculosis.

EXAMPLE 5

Identification of Mycobacteria by Mass Spectrometry Directly from the Liquid Medium The identification of mycobacteria from a culture in liquid medium is based at present on Ziehl staining, then molecular identification according to various methods published in the literature. The limitations of these methods are their time of several hours (between 4 and 24 hours) and their cost. The inventors envisaged utilizing identification of bacteria by analysis of the protein profile by mass spectrometry, for rapid identification of *Mycobacterium tuberculosis* directly from the supernatant from the culture flask according to one of the media of the invention. In fact, analysis of protein profiles by mass spectrometry has so far only been developed for strains of mycobacteria isolated and cultured in solid medium and not for cultures of biological samples comprising mycobacteria cultured in solid or liquid medium [Hettick J M, Kashon M L, Simpson J P, Siegel P D, Mazurek G H, Weissman D N. Proteomic profiling of intact mycobacteria by matrix-assisted laser desorption/ionization time-of-flight mass spectrometry. Anal Chem. 2004; 76:5769-76; Hettick J M, Kashon M L, Slaven J E, Ma Y, Simpson J P, Siegel P D, Mazurek G N, Weissman D N. Discrimination of intact mycobacteria at the strain level: a combined MALDI-TOF MS and biostatistical analysis. Proteomics. 2006; 6:6416-25; Pignone M, Greth K M, Cooper J, Emerson D, Tang J. Identification of mycobacteria by matrix-assisted laser desorption ionization-time-of-flight mass spectrometry. J Clin Microbiol. 2006; 44:1963-70]. The use of mass spectrometry for rapid identification of *Mycobacterium tuberculosis* mycobacteria directly in their biological sample in culture came up against many difficulties connected with the need to inactivate the mycobacteria once the sample is collected in the bottle of liquid culture, without altering their protein profile. Several protocols, using for example inactivation of mycobacteria in the culture medium with 2.5% trifluoroacetic acid (TFA) or with 1% glutaraldehyde did not provide a discriminating spectrum. Finally, the inventors obtained identification spectra using a protocol of heat inactivation as detailed below:

The protocol for preparation of the culture media, for detection and identification of the mycobacteria in the media of the invention by mass spectrometry, was as follows:

1- in a laboratory of safety level P3, take 5 ml of supernatant from the culture bottle in five sterile tubes (1 ml per tube)

2- heat for 1 h at 95° C.

3- take out of the P3 laboratory 4- centrifuge at low speed 500 rev/min for 15 min 5- recover the supernatant from each of the five tubes in a new sterile tube 6- centrifuge the supernatant at high speed 14000 rev/min for 10 minutes 7- discard the supernatant 8- wash the pellet with 1 ml of PBS 9- centrifuge at 14000 rev/min for 10 minutes 10- discard the supernatant 11- add 5 μL of 20% trifluoroacetic acid (TFA)

12- add 5 μl of 100% acetonitrile 13- wait 10 min 14- vortex 15- deposit 1 μl of the mixture on the spectrometry plate 16- leave to dry 17- deposit 1 μl of matrix solution 18- leave to dry 19- submit the plate to mass spectrometry.

For each sample, the inventors made four deposits on the mass spectrometry plate in parallel. The deposits were covered with 2 μL of matrix solution, namely a saturated solution of alpha-cyano-4-hydroxycinnamic acid in acetonitrile at 50%, and of trifluoroacetic acid at 2.5%. The matrix solution was crystallized at room temperature for 5 minutes. The mass spectrometry analyses were performed using an Autoflex II spectrometer (Bruker Daltonik) equipped with a nitrogen laser with a wavelength of 337 nm. The spectra were recorded in linear mode (time 170 ns, ion source 1 (IS1) voltage 20 kV; ion source 2 (IS2) voltage 18.5 kV; lens voltage 7 kV; molecular weight between 2 and 20 kDa). Each spectrum was obtained after 675 firings in automatic mode with variable laser power and an acquisition time of 30-60 seconds per deposit. Automatic data acquisition was provided by AutoXecute acquisition control software. For each sample, the four spectra obtained were imported into BioTyper version 2.0 software (Bruker Daltonik GmbH) and were analyzed using the default parameters. The spectra were compared with a local bank of spectra of the mycobacteria prepared by the inventors. The species of mycobacteria were selected to be representative of the groups/species mostly found in human pathology in the literature and in the inventors' experience, namely *Mycobacterium avium* ss avium, *Mycobaterium avium* ss paratuberculosis as slow-growing *mycobacterium* and *Mycobacterium smegmalis* as quick-growing *mycobacterium*. The method of analysis included m/z ratios between 3 and 15 kDa.

FIGS. 7A to 7D show spectra obtained in mass spectrometry from culture in liquid medium according to the invention, for different strains of mycobacteria.

Figure 7A:
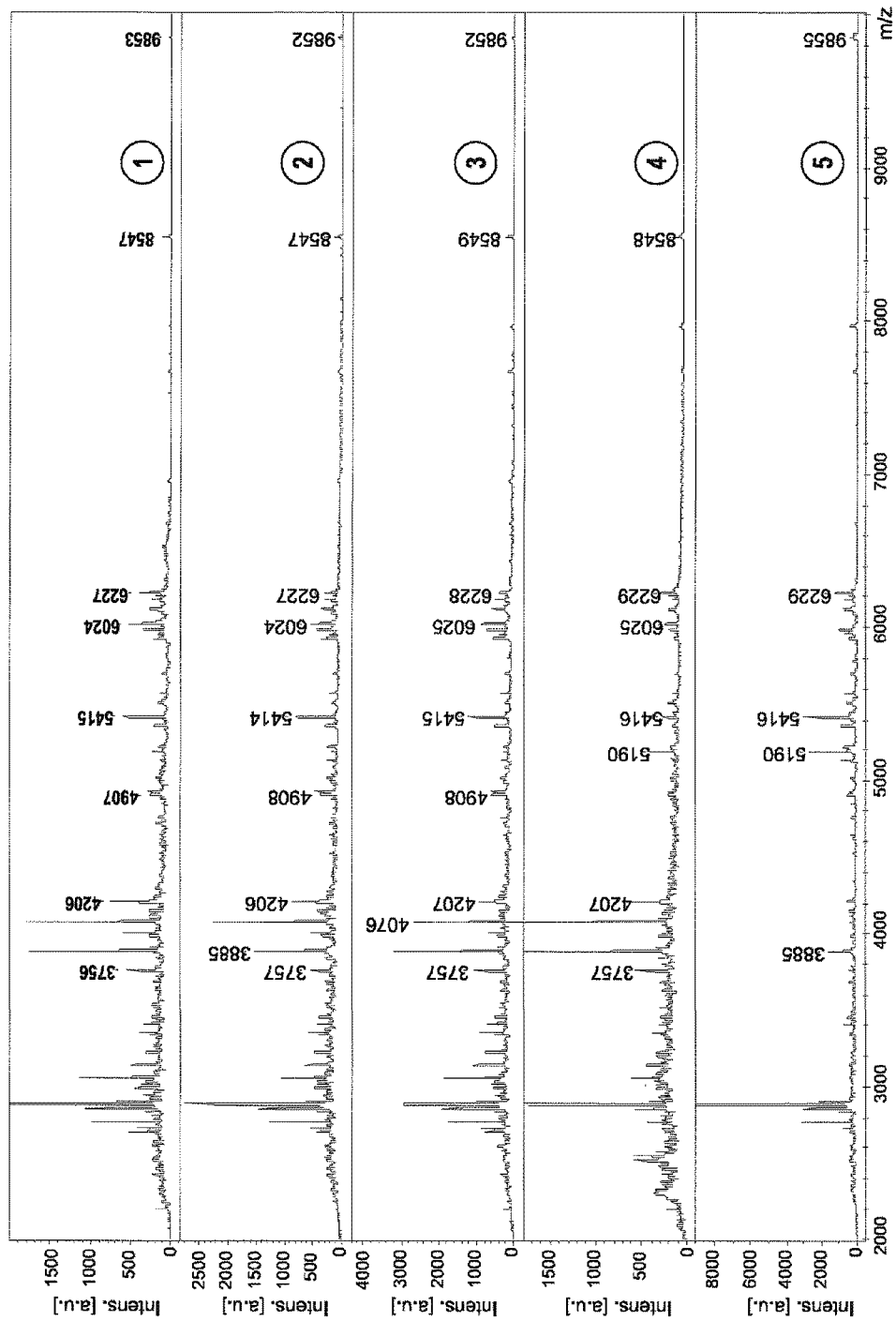
FIGS. 7A and 7B show spectra obtained by mass spectrometry in example 5.
Figure 7B:
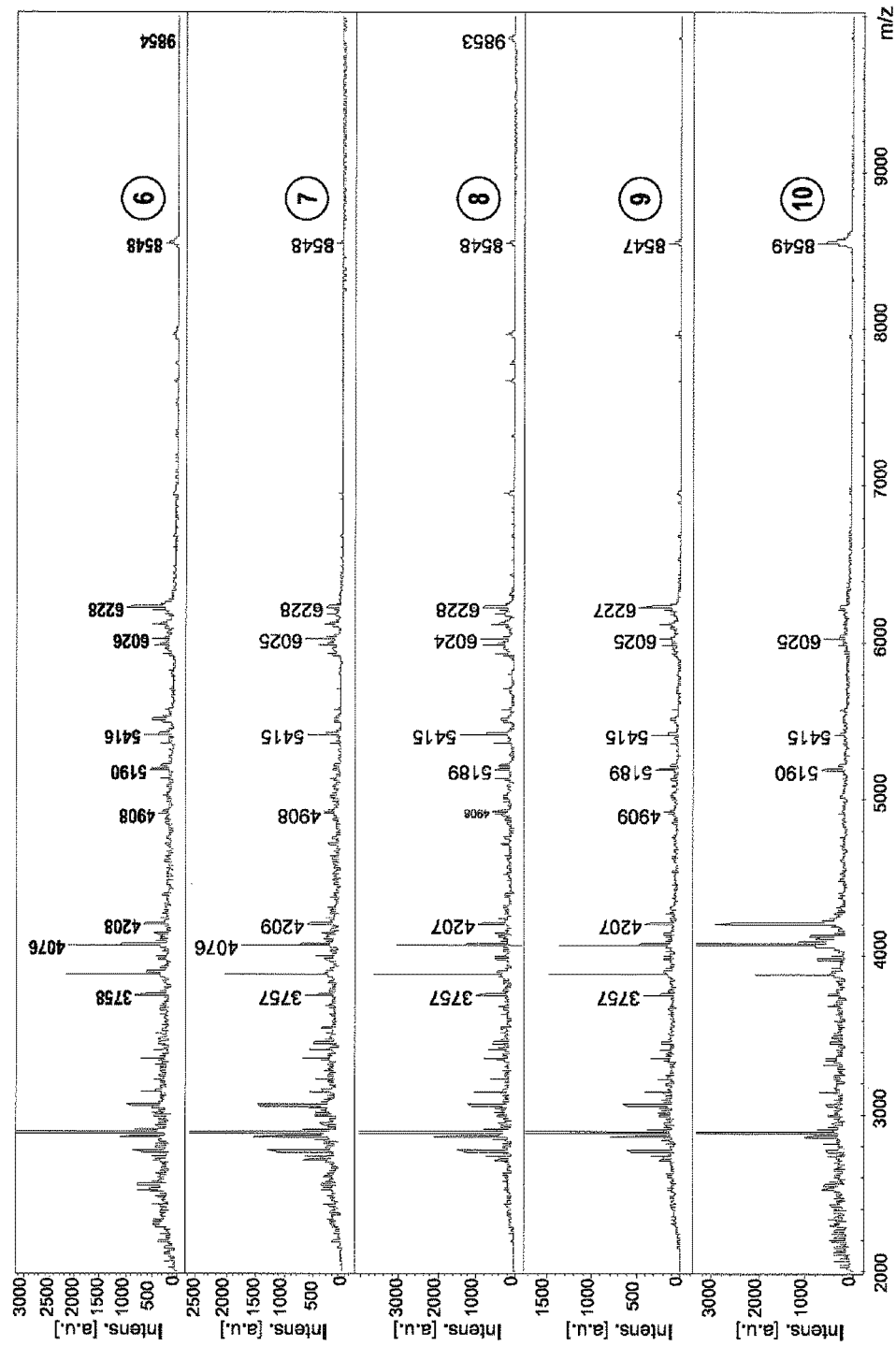
Figure 7C:
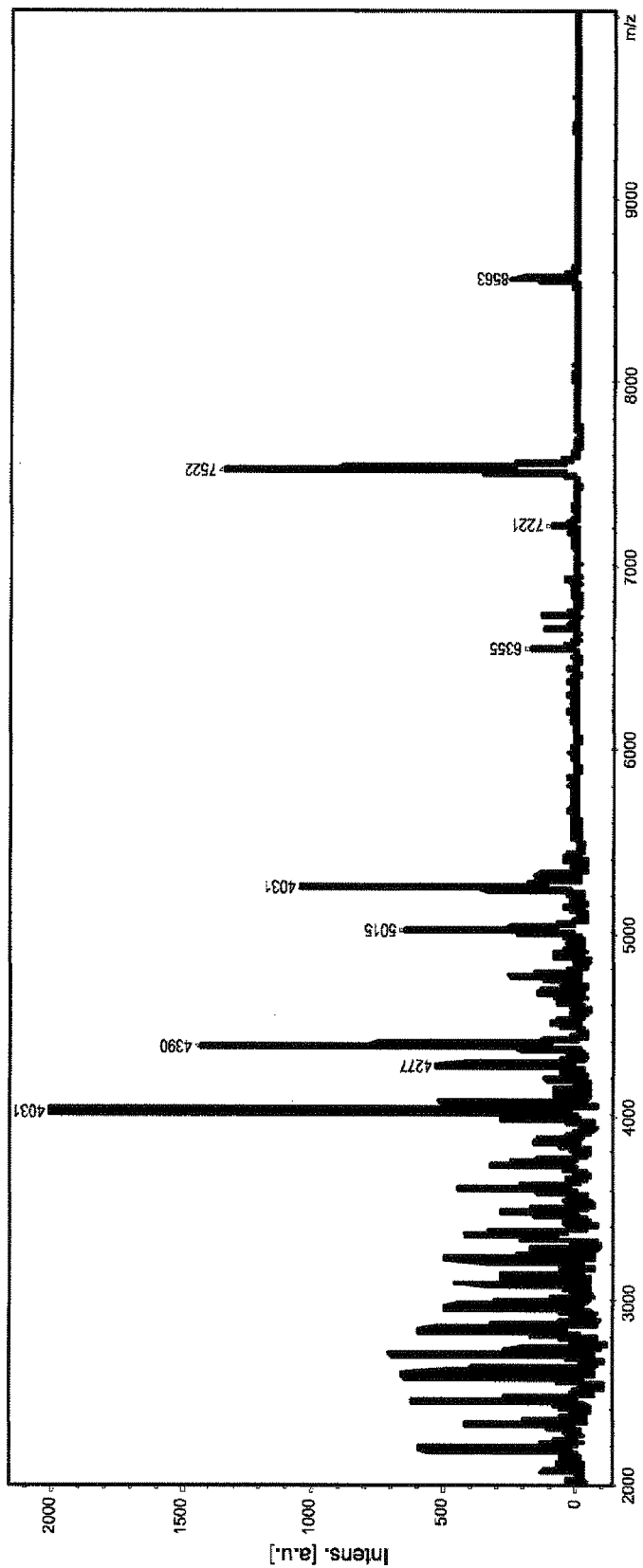
FIG. 7C shows a negative control spectrum obtained from the uninoculated liquid medium B25% and, for comparison.

FIGS. 7A and 7B show protein spectra obtained by mass spectrometry from 10 clinical strains of *Mycobacterium tuberculosis* cultured in a liquid medium B25% according to the invention. FIG. 7C shows a negative control spectrum obtained from the same, uninoculated liquid medium B25% and, for comparison, FIG. 7D shows spectra obtained from the same liquid medium B25% according to the invention inoculated with *Mycobacterium avium* ss. avium (11), *Mycobacterium avium* ss. paratuberculosis (12) and *Mycobacterium smegmatis* (13).

Figure 7D:
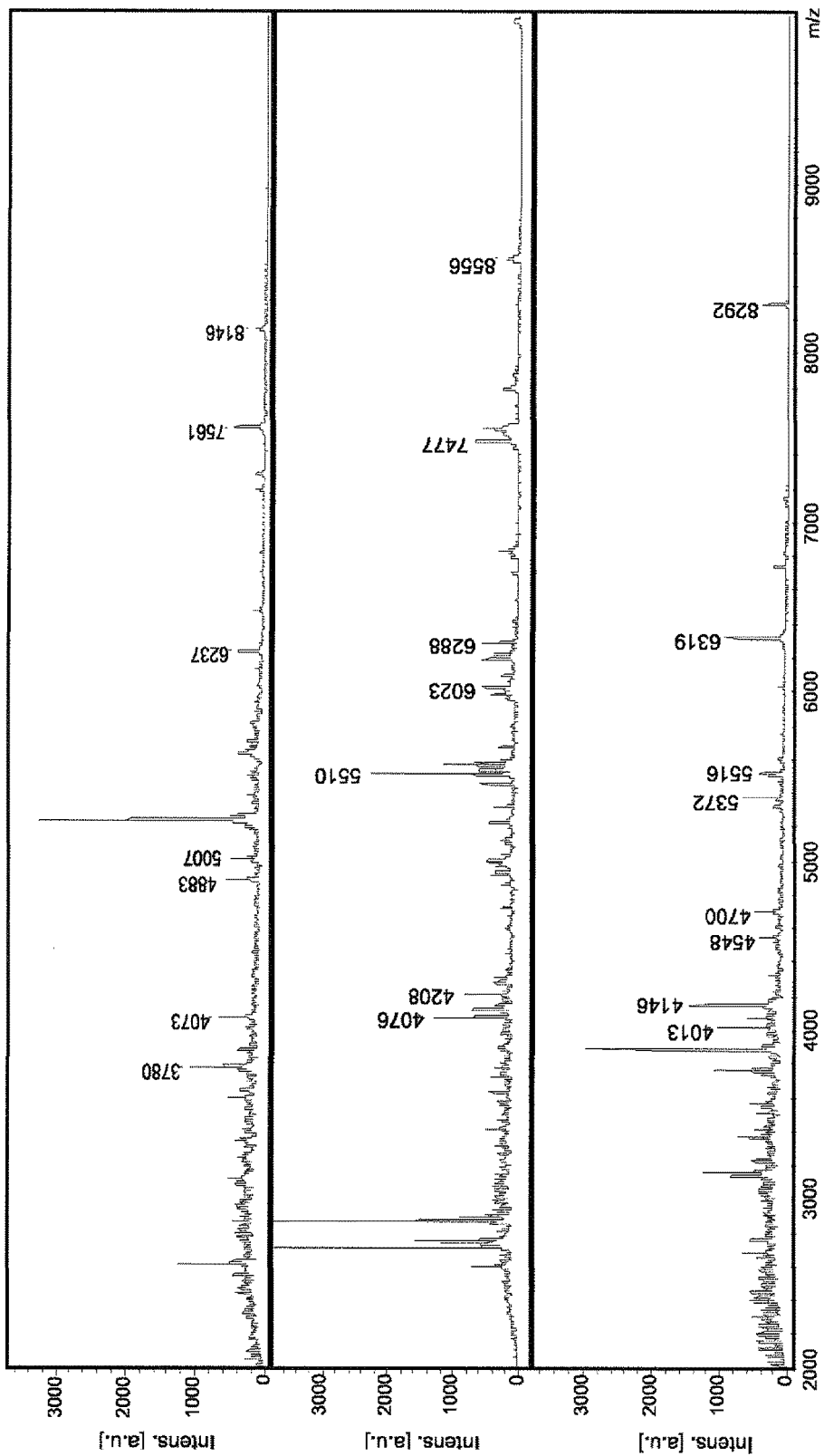
FIG. 7D shows spectra obtained from the liquid medium B25% according to the invention inoculated with *Mycobacterium avium* ss. *avium*, *Mycobacterium avium* ss. Paratuberculosis, and *Mycobacterium smegmatis*.
Figure 8A:
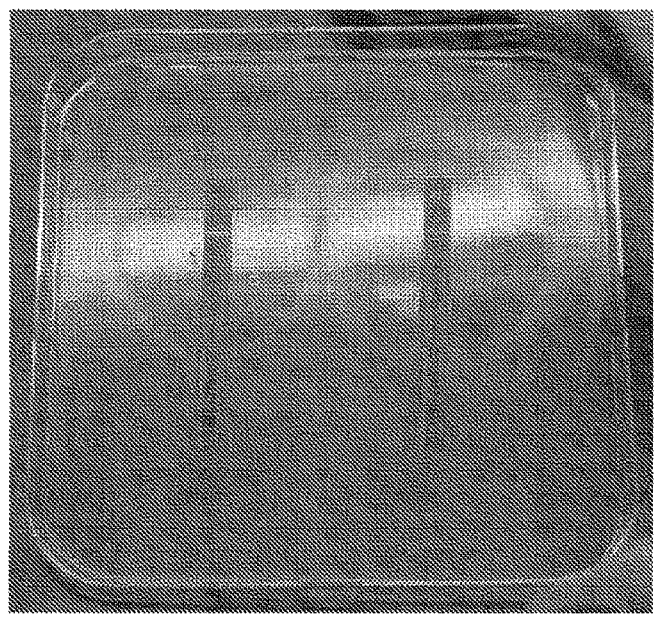
FIGS. 8A and 8B show photographs of bacterial growth on a reference solid culture medium (FIG. 8A) and a solid culture medium according to the invention (FIG. 8B) in contact with strips of blotting paper impregnated with antibiotic.
Figure 8B:
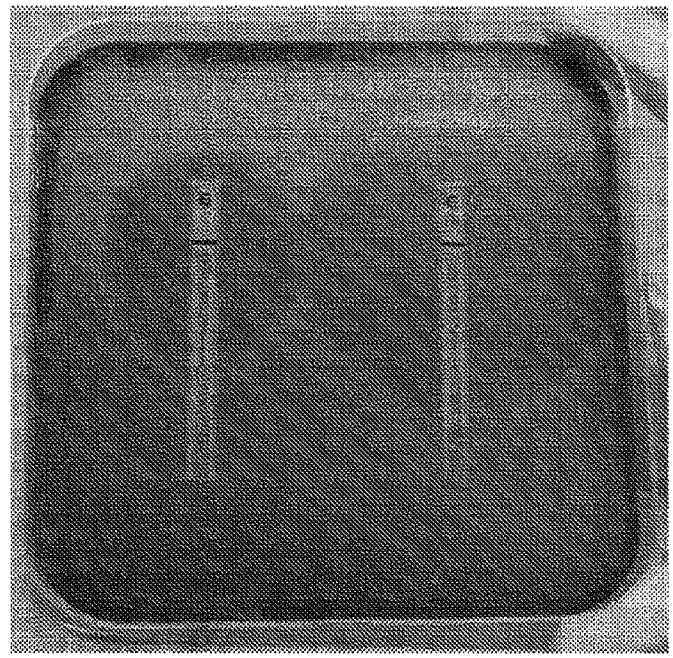

The spectra in FIGS. 7A and 7B, for the different aforementioned strains of the same species *Mycobacterium tuberculosis*, display a profile that is extremely reproducible from one strain to another and, moreover, different from that of the strains of the other species of mycobacteria of FIG. 7D, on the one hand, and different from the control in FIG. 7C, on the other hand.

Comparing the spectra in FIGS. 7A to 7D, it is observed that for *Mycobacterium tuberculosis*, peaks are obtained specifically, corresponding to the four proteins having the following molecular weights (in dalton): 8548±1; 6228±1; 6025±1; 5415±1.

The protocol for preparation of the culture media for detection and identification of the mycobacteria in the solid media of the invention by mass spectrometry was as follows:

1- take 1 ml of supernatant from the bottle, previously agitated, in a sterile tube
2- inactivate the mycobacteria by heating at 95° C. for 1 hour
3- centrifuge at low speed 500 rpm for 15 minutes
4- recover the supernatant in a new sterile tube
5- centrifuge the supernatant at 14000 rev/min for 10 minutes
6- discard the supernatant
7- wash the pellet with 1 ml of buffer solution PBS
8- centrifuge at 14000 rpm for 10 minutes
9- discard the supernatant
10- add 5 µL of 20% TFA
11- add 5 µl of 100% acetonitrile
12- wait 10 minutes
13- vortex
14- deposit 1 µl of the mixture on the spectrometry plate
15- leave to dry
16- deposit 1 µl of matrix solution
17- leave to dry for 10 minutes at room temperature
18- submit the plate to mass spectrometry.

All the manipulations must be carried out in full safety gear (cap, mask, over-jacket and gloves) under a hood.

EXAMPLE 6

Phenotypic Determination of the Sensitivity of *M. Tuberculosis* to Antibiotics a/- Methods:

The inventors tested six clinical strains of the species *Mycobacterium tuberculosis* isolated from respiratory samples during routine diagnostics in their clinical microbiology laboratory. These six strains were identified as being of the species *Mycobacterium tuberculosis* by their characteristic morphology in strands after Ziehl staining, then by PCR amplification and sequencing of intergenic spacers [Djelouadji Z et al. A Single-Step Sequencing Method for Identification of *Mycobacterium tuberculosis* Complex Species. PLoS Negl Trop Dis. 2008 Jun. 18; 2(6):e253]. These six strains tested sensitive to the first-line antituberculous antibiotics using a reference phenotypic test in solid medium, only testing the so-called critical concentrations for each of the four antibiotics tested: isoniazid, 0.2 μg/ml; rifampicin, 1 μg/ml; ethambutol, 5 μg/ml and streptomycin, 5 μg/ml. [Woods G L, Warren N G, Inderlind C B. Susceptibility test methods: Mycobacteria, Nocardia, and other Actinomycetes in: Manual of Clinical Microbiology, 9th edition (Nurray P R, Baren E J, Jorgensen J H, Bry N L, Pfaller M A. American Society for Microbiology, 2007, page 1223-1247]. A clinical strain resistant to antituberculous drugs (minimum inhibitory concentration of rifampicin >1 μg/ml) as determined by the reference method in solid medium, was tested in parallel [Woods G L, Warren N G, Inderlind C B. Susceptibility test methods: Mycobacteria, Nocardia, and other Actinomycetes in: Manual of Clinical Microbiology, 9th edition (Nurray P R, Baren E J, Jorgensen J H, Bry N L, Pfaller M A. American Society for Microbiology, 2007, page 1223-1247). These strains were suspended in sterile phosphate buffer at a concentration of $10^6$ colonies/ml. This suspension was used in parallel for flooding a sterile Petri dish containing the reference standard medium: Middlebrook 7H10 medium supplemented with a mixture of oleic acid, albumin, dextrose, and catalase (OADC) and a sterile Petri dish containing the 15% solid medium according to the invention from example 2B above.

The inventors used the system called E-Test® (Biomerieux, France) for determining the sensitivity of the strains to the various antibiotics. This system is composed of a strip of paper impregnated with antibiotic (isoniazid or ethambutol) according to a continuous concentration gradient along the strip. This device permits naked-eye reading of the concentration starting from which growth of *Mycobacterium tuberculosis* is no longer observed, thus defining the minimum inhibitory concentration of antibiotic (isoniazid or ethambutol) with respect to the strain of *Mycobacterium tuberculosis* being tested. The Petri dishes were incubated at 37° C. in an atmosphere containing 5% $CO_2$ for two weeks with observation daily starting from the sixth day of incubation. The colonies were confirmed as being *Mycobacterium tuberculosis* on the basis of their appearance and, after Ziehl staining, showing strands of alcohol-acid-resistant bacilli. There is formation of a disk of inhibition of bacterial growth around the strip in the zones containing a concentration of antibiotic above the minimum inhibitory concentration, it being understood that the latter is determined by the intersection of the disk of inhibition with the strip.

b/- Results:

The inventors observed that:

(1) colonies of *Mycobacterium tuberculosis* appeared after 7 days of incubation on the medium according to the invention and after 11 days of incubation on the reference medium, (2) reading of the E-test is possible in these conditions after 7 days of incubation on the medium according to the invention as there is a sufficient number of colonies to permit reading and a very good contrast between the colonies, which appear gray on the red background of the medium according to the invention; whereas reading is only partial and difficult after 11 days of incubation on the reference medium, because of incomplete growth of the colonies on the reference medium and poor contrast between the color of the colony (translucent) and the reference medium, (3) the results of the E-tests isoniazid and ethambutol obtained on the medium according to the invention are similar to those obtained beforehand by the reference method, (4) the results of the E-tests isoniazid and ethambutol obtained on the medium according to the invention are more accurate than those of the reference tests, permitting determination of a true minimum inhibitory concentration.

This experiment demonstrates that, by using a solid medium according to the invention, phenotypic tests of the sensitivity of *Mycobacterium tuberculosis* to the antituberculous drugs according to the E-test method can be carried out more quickly and more easily than execution of the E-test on a solid reference medium.

FIGS. 8A and 8B show photographs of a Petri dish containing the reference medium (FIG. 8A) and the medium according to the invention (FIG. 8B), incubated after inoculation of one and the same strain of the species *Mycobacterium tuberculosis*, showing the presence of colonies of *Mycobacterium tuberculosis* that are easily visible after 7 days on the medium according to the invention (FIG. 8B) and are difficult to see on the reference medium after 11 days (FIG. 8A), permitting easy reading of the inhibitory concentration of isoniazid (IZ) on a first strip and ethambutol (ET) on a second strip.

In FIGS. 8A and 8B, we can see, around the strips, zones of inhibition of bacterial growth in the form of an oval disk around parts of the strip containing an inhibitory concentration of antibiotic, so that intersection of the lower limit of said inhibitory zones with the strips makes it possible to read, on the graduated strip, the minimum inhibitory concentration of the antibiotic.

The invention claimed is:

1. A culture medium for mycobacteria, comprising:

growth factors for mycobacteria, antibiotics without activity against mycobacteria, lecithin in a proportion by weight of from 0.1 to 5%, and defibrinated blood in a proportion by volume of from 2.5 to 15%, and decomplemented fetal calf serum in a proportion by volume of from 2.5 to 25%.

2. The culture medium for mycobacteria as claimed in claim 1, wherein:

the lecithin is egg yolk lecithin, and the blood is defibrinated rabbit or sheep blood.

3. The culture medium for mycobacteria as claimed in claim 1, wherein said culture medium comprises a basic culture medium for mycobacteria comprising, besides distilled water, the following components: ammonium sulfate, magnesium sulfate, copper sulfate, zinc sulfate, sodium citrate, ferric ammonium citrate, sodium chloride, calcium chloride, monopotassium phosphate, disodium phosphate, L-glutamic acid, biotin and pyridoxine.

4. The culture medium for mycobacteria as claimed in claim 1, wherein said culture medium is a liquid culture medium.

5. The culture medium for mycobacteria as claimed in claim 4, wherein said culture medium comprises a basic culture medium which is a Middlebrook liquid medium of reference 7H9 and the following additional growth factors for mycobacteria: casein hydrolyzate, glycerol, polysorbate, hemin, lactic acid, biotin, polyoxyethylene stearate, bovine serum albumin, dextrose and supplement H.

6. The culture medium for mycobacteria as claimed in claim 1, wherein said culture medium is a solid culture medium containing a gelling agent.

7. The culture medium for mycobacteria as claimed in claim 6, wherein said culture medium is a solid medium of the Middlebrook type of reference 7H10, with addition of said gelling agent and the following additional growth factors for mycobacteria: oleic acid, bovine albumin, dextrose, catalase and glycerol.

8. The culture medium for mycobacteria as claimed in claim 1, wherein lecithin is contained in a proportion by weight from 0.5 to 1%.

9. The culture medium for mycobacteria as claimed in claim 8, wherein said culture medium is a solid culture medium containing a gelling agent selected from agars in a proportion by weight from 0.5 to 5%.

10. The culture medium for mycobacteria as claimed in claim 1, wherein the blood is contained in a proportion by volume from 5 to 10%.

11. The culture medium for mycobacteria as claimed in claim 1, wherein decomplemented fetal calf serum is contained in a proportion by volume from 10 to 20%.

* * * * *

UNITED STATES PATENT AND TRADEMARK OFFICE
CERTIFICATE OF CORRECTION

PATENT NO. : 8,841,087 B2  
APPLICATION NO. : 13/131921  
DATED : September 23, 2014  
INVENTOR(S) : Michel Drancourt et al.

Page 1 of 1

It is certified that error appears in the above-identified patent and that said Letters Patent is hereby corrected as shown below:

Title Page

(75) Inventors should read: Michel Drancourt, Marseille (FR);
Didier Raoult, Marseille (FR)

Signed and Sealed this
Twenty-first Day of April, 2015

Michelle K. Lee
*Director of the United States Patent and Trademark Office*